United States Patent
Launay et al.

(10) Patent No.: US 6,224,257 B1
(45) Date of Patent: May 1, 2001

(54) DEVICE FOR SIMULATING A PATIENT'S BLOOD VESSELS

(76) Inventors: Laurant Launay, 35, rue de l'Orangerie, 78000 Versailles; Rene Romeas, 23, rue du Hameau des joncherettes; Yves Lucien Marie Trousset, 8, residence du Parc, both of 91120 Palaiseau; Regis Vaillant, 3, place Rabelais, 91140 Villebon sur Yvette, all of (FR)

(*) Notice: Subject to any disclaimer, the term of this patent is extended or adjusted under 35 U.S.C. 154(b) by 0 days.

(21) Appl. No.: 09/325,368

(22) Filed: Jun. 4, 1999

(30) Foreign Application Priority Data

Jun. 5, 1998 (FR) .................................................. 98 07115

(51) Int. Cl.[7] .................................................. G01D 18/00
(52) U.S. Cl. .......................... 378/207; 378/18; 350/252.1
(58) Field of Search .......................... 250/252.1; 378/207, 378/18

(56) References Cited

U.S. PATENT DOCUMENTS

| 4,618,978 | 10/1986 | Cosman | 378/164 |
|---|---|---|---|
| 4,649,561 * | 3/1987 | Arnold | 378/207 |
| 4,794,631 * | 12/1988 | Ridge | 378/207 |
| 4,838,265 | 6/1989 | Cosman et al. | 128/203 |
| 5,236,363 * | 8/1993 | Sandrik et al. | 434/267 |
| 5,442,674 | 8/1995 | Picard et al. | 378/20 |
| 5,544,157 * | 8/1996 | Wenstrup et al. | 378/18 |
| 5,712,895 | 1/1998 | Negrelli et al. | 378/207 |

FOREIGN PATENT DOCUMENTS 9723164  7/1997  (WO).

* cited by examiner

*Primary Examiner*—David V. Bruce
*Assistant Examiner*—Allen C. Ho
(74) *Attorney, Agent, or Firm*—Jay L. Chaskin

(57) ABSTRACT

Device for simulating a patient's body for the testing of a vascular X-ray apparatus of the type comprising a means for emitting an X-ray beam, and a means for receiving the X-ray beam after it has passed through a part of the patient's body, the X-ray beam being centered on an axis. The device comprises at least one metal wire disposed at least partially transversely relative.

11 Claims, 4 Drawing Sheets

DEVICE FOR SIMULATING A PATIENT'S BLOOD VESSELS

BACKGROUND OF THE INVENTION

The present invention belongs to the field of devices that make it possible to simulate the body or a part of the body, particularly a patient's blood vessels, for the testing of an X-ray apparatus.

An X-ray apparatus generally comprises a tube that allows the emission of an X-ray beam in a given direction, means for positioning at least one part of a patient's body in the X-ray beam, and receiving means that sense the X-rays disposed in the beam after it has passed through the patient's body part. An X-ray apparatus requires the control of many parameters that can deviate over the course of time, which requires maintenance interventions at regular intervals. The reduction in the quality of the images obtained by the receiving means can be linked, for example, to slight changes in the geometry of the apparatus due to wear on the parts, or to variations in the magnetic field surrounding the apparatus.

In order to characterize such deviations, it is necessary to obtain a device that makes it possible to simulate the body of a patient. The display of the simulation device on a screen takes place in a way that is identical to that of the patient's body, and makes it possible to reveal possible deviations and thus to determine whether the X-ray apparatus is working with a precision greater than the minimal precision required or whether, on the contrary, the X-ray apparatus should undergo a maintenance operation in order to restore the precision of the images obtained.

Simulation devices of this type are particularly useful in the field of vascular imaging by image subtraction. The blood vessels of the human body being naturally transparent to X-rays, an image is first taken without the addition of an opacifying product, after which an opacifying product, for example iodine-based, is injected into the patient's blood, which makes the blood opaque to X-rays, then a second image is taken after the opacifying product has been properly distributed through the patient's vascular network. The two images or series of images obtained being numbered by electronic means, an image subtraction is then carried out, making it possible to remove from the second image the organs visible in the first one, i.e., the organs naturally visible to X-rays such as the bones, etc.

BRIEF SUMMARY OF THE INVENTION

The present invention provides a simulation device that is easy to handle while being adaptable to various types of X-ray apparatuses. It is more particularly adapted to the testing of three-dimensional imaging apparatuses.

The device for simulating a patient's body is intended for the testing of a vascular X-ray apparatus of the type comprising a means for emitting an X-ray beam, and a means for receiving the X-ray beam after it has passed through a part of the patient's body, the X-ray beam being centered on an axis and rotatable. The simulation device comprises at least one metal wire disposed at least partially transversely relative to the axis.

In one embodiment of the invention, the wire is disposed helicoidally relative to the axis normal to the plane of rotation of the axis of the X-ray beam. Each wire can be disposed on a spire. Preferably, the wires have diameters that are different from one another. Each wire can be disposed at a distance from the axis normal to the plane of rotation of the axis of the X-ray beam that is different from that of the other wires.

In one embodiment of the invention, each wire is disposed on a support with a shape adapted to the shape of the means for receiving the X-ray ray beam. The support can be cubical or spherical with a polygonal equatorial section.

In one embodiment of the invention, the support comprises elements with low X-ray absorption to which the wires are attached, said elements extending from one end of the support to the other.

In one embodiment of the invention, the support comprises a central shaft perpendicular to the axis and made of a material with average X-ray absorption.

BRIEF DESCRIPTION OF THE DRAWINGS

The present invention will be more clearly understood through the study of the detailed description of one embodiment, taken as a non-limiting example and illustrated by the attached drawings, in which.

DETAILED DESCRIPTION OF THE INVENTION

The simulation operation can be carried out in the following way: at least one image is acquired of a unit for simulating the patient's bones and soft tissue only, and at least one image is acquired of this unit and of the device for simulating the patient's opacified blood vessels, and using image subtraction, an image of the simulation device is obtained. This simulation device is optimized so as to be sensitive to the slightest error of the X-ray apparatus and to allow its detection.

In a three-dimensional angiography system with C-shaped arms, it is possible to acquire images of the blood vessels while the acquisition system, i.e., the X-ray tube and the means for receiving the X-ray beam, rotates around the patient. A three-dimensional image of the vessels is then reconstructed from the series of two-dimensional digital images produced. In order to perform this reconstruction, a model of the geometry of the image acquisition is necessary. This model is estimated in a calibration phase, and it is subsequently determined whether the acquisition geometry is the same during the acquisition of the images of the patient as it was during the calibration. If the acquisition geometry is not exactly the same, i.e., if the performance of the acquisition system is degraded, the quality of the reconstructed three-dimensional images will also be degraded: the vessels will less rich in contrast and certain vessels of small diameter will not be properly reconstructed or will appear blurry.

Measuring the performance level of the acquisition system for the reconstruction of three-dimensional images is important, both during the production of the X-ray apparatus and while it is in service, but it constitutes a relatively difficult operation. In fact, a poor image quality observed on a patient is not invariably due to the acquisition system. Many other parameters can be involved, such as a movement of the patient, the propagation of the opacifying liquid that is injected into the patient's bloodstream, etc. An error in the repositioning of the acquisition system is not easy to detect. An element of the display device can be different for an acquisition of an image of the patient and for the calibration that was done previously, even though the quality of the two-dimensional images derived from the acquisition of images of the patient may be perfectly acceptable.

In order to control the performance level of a three-dimensional angiography system, it is necessary to simulate a rotating acquisition of images of the patient with a specific simulation device, also called a "phantom." The images of this phantom must be representative of the patient's blood vessels.

Figure 1:
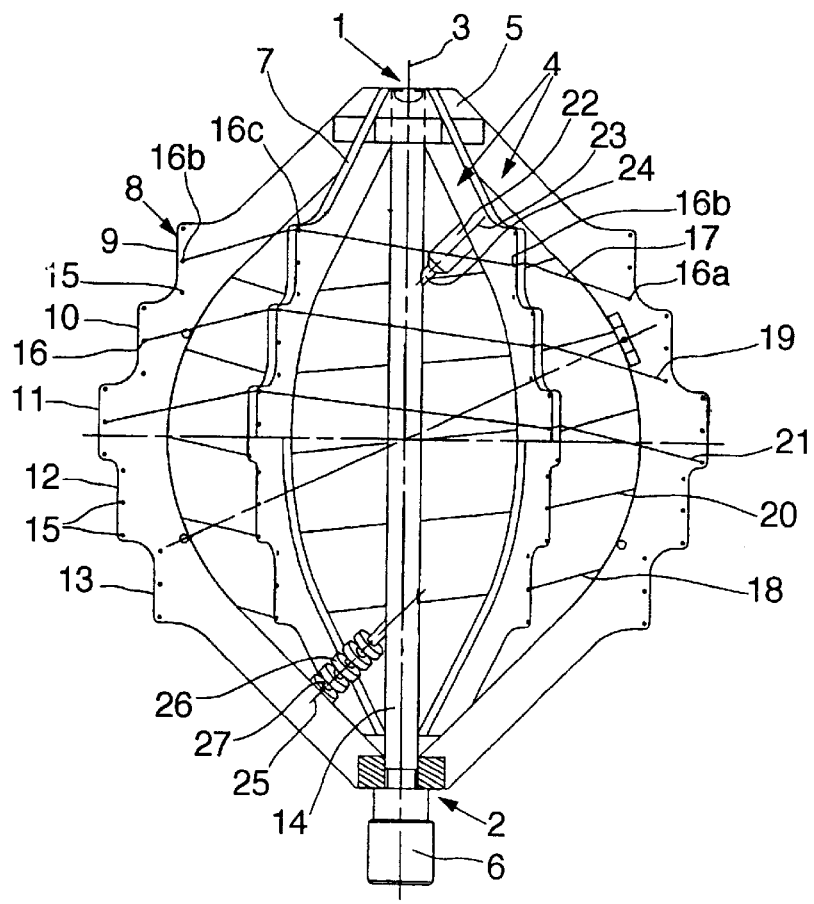
FIG. 1 is a side elevation of a simulation device according to an embodiment of the invention.
Figure 2:
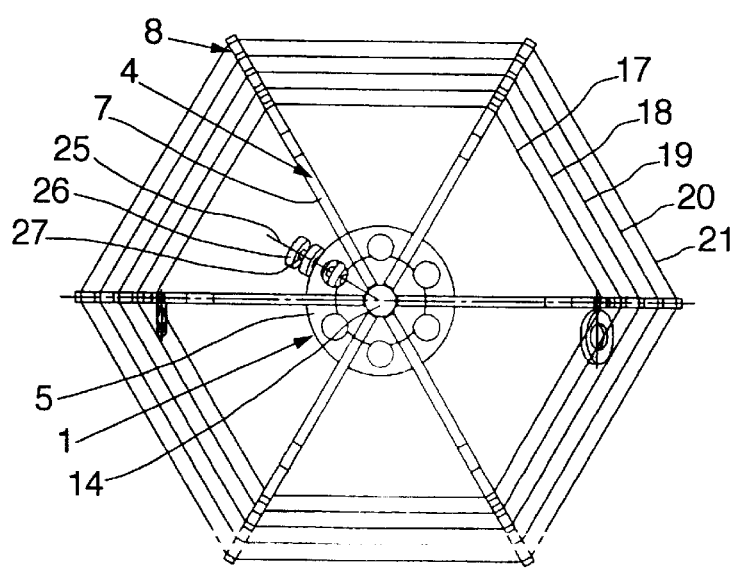
FIG. 2 is a top view of the device of FIG. 1.

As seen in FIGS. 1 and 2, the simulation device has a generally spherical shape with a top pole 1 and a bottom pole 2, centered on an axis 3 represented in a broken line, and comprises semicircular elements 4 extending from the top pole 1 to the bottom pole 2. A supporting piece 5 is provided at the top pole 1 and a supporting piece 6 is provided at the bottom pole 2. The semicircular elements 4 are attached at each of their ends to the supporting piece 5 and the supporting piece 6. The semi-circular elements 4 are made of a material with low X-ray absorption, for example plexiglas, polycarbonate, or another material of equiva-lent density. The simulation device comprises six semicircular elements 4 distributed uniformly in the circumferential direction. However, as a variant, it is possible to provide a different number, for example four or eight.

The semicircular elements 4 are flat and have on their outer edge 7 a tiered area 8 comprising steps 9 through 13 whose distance from the axis 3 differs from one step to another. A central shaft 14 coaxial to the axis 3 connects the supporting pieces 5 and 6 of the top 1 and bottom 2 poles. The central shaft 14 ensures the mechanical strength of the entire simulation device and is made of a material with average X-ray absorption, for example aluminum. As a variant, it is possible to provide a central shaft 14 made of another material, for example ceramic or titanium, but with the respective drawbacks in terms of weight and cost.

The semicircular elements 4 are pierced with a plurality of holes 15 and 16 of small diameter, passing through the thickness of the semicircular elements 4 and disposed perpendicular to a plane passing through the axis 3 near the outer edge 7 at the level of the steps 9 through 13.

Wires labelled 17 through 21 are passed through the holes 16, the holes 15 remaining free of wires. The wires 17 through 21 are each disposed on one complete spire of the simulation device so as to form an angle on the order of 15° with a radial plane. For example, the wire 17 that passes through the holes 16 of the step 9 of the various semicircular elements 4, passes through the hole 16a provided at the bottom of the step 9 of the semicircular element 4 visible on the right of FIG. 1, then through the hole 16b in the middle of the step 9 of the next semicircular element 4, then through the hole 16c of the next semicircular element 4 before passing through the hole 16b in the middle of the step 9 of the semicircular element 4 visible on the left of FIG. 1. Of course, the concepts of right and left, and top and bottom, are relative and refer to FIG. 1, since the simulation device can be used in any position in space. The other wires 18 through 21 are disposed in similar fashion through the holes 16 of the other steps 10 through 13.

The wires 17 through 21 are made of copper, a material with high X-ray absorption, but could also be made of another metal or alloy, as long as their diameter is adapted in accordance with the X-ray absorption of the material. The diameters of the wires are uniformly graduated, between 0.2 and 0.6 mm. The ends of the wires 17 through 21 are passed through a hole 16 and fixed with a dot of adhesive.

Extending from the central shaft 14 is a cylindrical element 22 disposed on an axis 23 that is oblique relative to the axis 3. The cylindrical element 22 is connected to the central shaft 14 by a portion 24 of small diameter. The cylindrical element 22 is also made of a material with high X-ray absorption and makes it possible to simulate an aneurysm, which often has a neck of reduced diameter, simulated by the portion 24.

The central shaft 14 also supports a ringed element 25 disposed obliquely relative to the central shaft 14 and provided with a succession of portions 26 of large diameter and portions 27 of small diameter, in order to make it possible to verify whether said portions 26 and 27 are displayed satisfactorily.

As seen more particularly in FIG. 2, the semicircular elements 4 are uniformly distributed in the circumferential direction so that the wires 17 through 21 form a hexagon approaching a spherical shape, which is particularly well adapted to the case where the field of vision of a camera of the X-ray apparatus is circular. It would also be possible to provide a simulation device with eight semi-circular elements defining an octagon, or even four or five semicircular elements defining a square or a pentagon.

Thus, the central shaft 14, with a large diameter relative to that of the wires 17 through 21 and an average X-ray absorption makes it possible to simulate the vessels of large diameter such as the carotid arteries and to provide a density reference for quantitative measurements from the reconstructed three-dimensional image. The large diameter of the central shaft 14 makes its image less sensitive to degradations. Thus, a stable reference is provided. The various wires 17 through 21 with a small diameter and a high X-ray absorption coefficient make it possible to simulate vessels of very small size, for example the small cerebral arteries, in order to estimate the resolution of the three-dimensional image reconstruction. The wires have various diameters, from 0.2 to 0.6 mm, in 0.1 mm increments. The distance between each wire and the central shaft 14 is determined so that the wires are as close as possible to the contour of the image in the two-dimensional projections, in order to obtain a satisfactory sensitivity to repositioning errors in the rotation of the camera of the X-ray apparatus, in the case of a camera that rotates around its axis.

The three-dimensional orientation of each wire is such that the angle between the axis of the wire and a plane that is radial relative to the axis 3 is small, less than or equal to 15°, but not null. In fact, if the wires were parallel to such a radial plane, the image would be extremely sensitive to the degradation of the quality, which is an advantage. The axis 3 is normal to the plane defined by the various positions of the axis of the X-ray beam, which is rotatable. But in certain incidences of two-dimensional projection, there would be a risk of superpositions of the horizontal wires, which would not make it possible to properly detect the errors. Thus, as seen in FIG. 1, certain wires 17 through 21 can cross at points, but are not superposed.

Likewise, as seen in FIG. 2, the wires 17 through 21, are disposed so as not to superpose one another. Of course, the same disposition of the wires could be obtained with a different support structure, for example with a polystyrene ball replacing the semicircular elements 4. During its utilization, the simulation device is positioned on a table of the X-ray apparatus on which the patient is normally disposed, in such a way that the central rod 14 is approximately parallel to the axis of rotation of the image acquisition system. The utilization of wires of different diameters and crossing one another facilitates the automation of the calibration process by counting the number of visible wires, the quality of the image being proportional to the number of visible wires.

Figure 3:
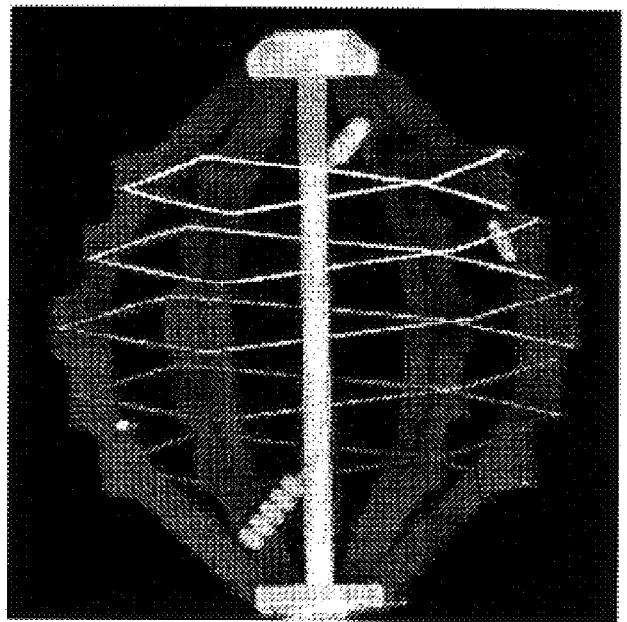
FIGS. 3 and 4 are three-dimensional reconstructions of images of the simulation device in the positions of FIGS. 1 and 2, respectively.
Figure 4:
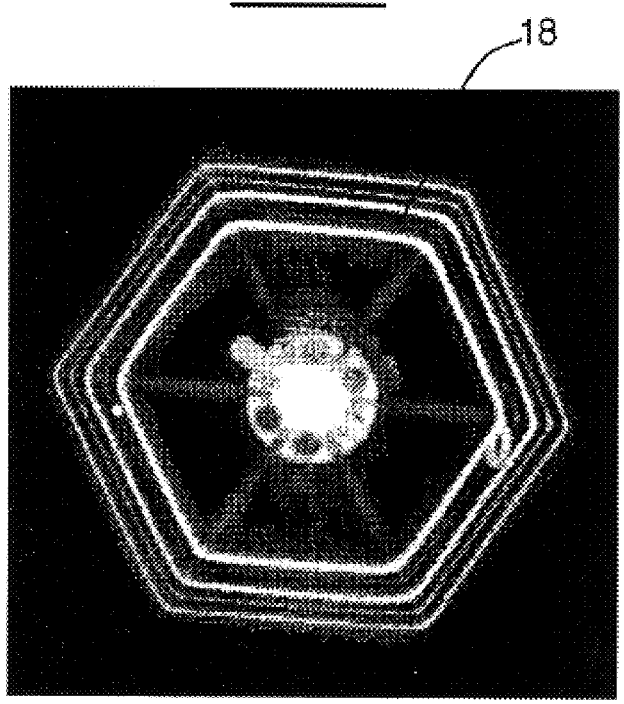

FIG. 3 shows a two-dimensional side view of a reconstructed three-dimensional image. It may be seen that all of the elements of the simulation device present in FIG. 1 are visible in FIG. 3. The wires of larger diameter appear more clearly than the wires of smaller diameter. The same is true of FIG. 4, which is a two-dimensional top view obtained from the same three-dimensional image used for FIG. 3. It is noted that the wire 18 of smaller diameter appears in this figure, which is a gauge of the good quality of the image reconstruction.

Figure 5:
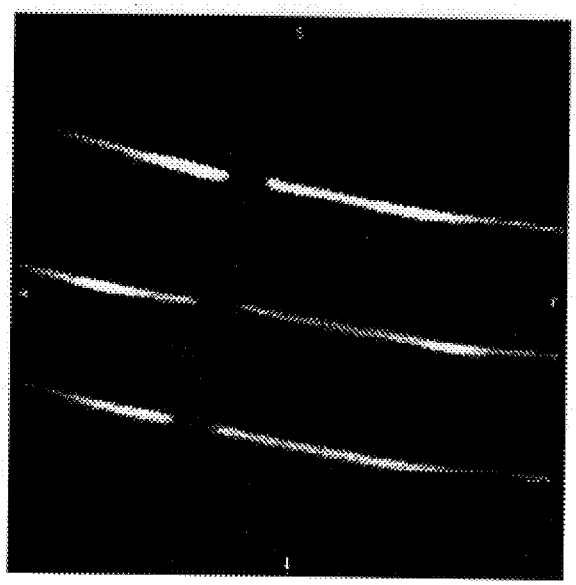
FIG. 5 is a schematic view of a cross-section of the simulation device in a plane passing through a wire portion.

FIG. 5 is a two-dimensional partial cross-section of the reconstructed three-dimensional image, in which appear portions of three adjacent wires, the image quality being satisfactory.

Figure 6:
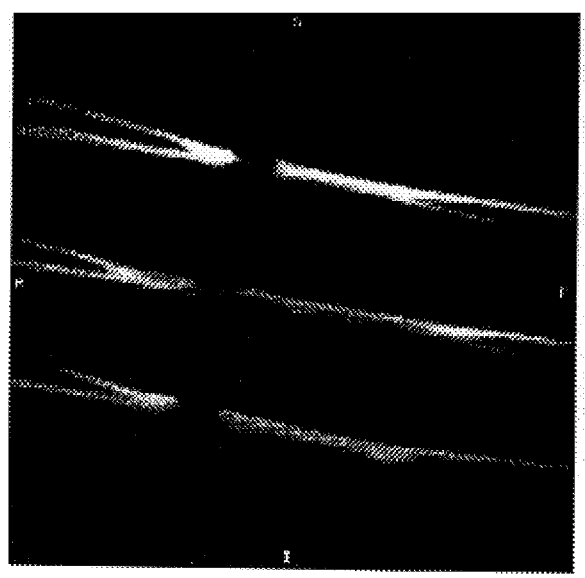
FIG. 6 is similar to FIG. 5, but with an error in the repositioning of the X-ray apparatus.

Conversely, in FIG. 6, which is a cross-section identical to that of FIG. 5, the image quality is not satisfactory in that the wires seem to divide in two. This degradation of the quality of the image is due to an error in the positioning of the arm supporting the X-ray tube and of the means for receiving and displaying incident X-rays, such as the scintillator, camera, CCD, etc. The repositioning error, in this case several tenths of a degree, is clearly shown.

Figure 7:
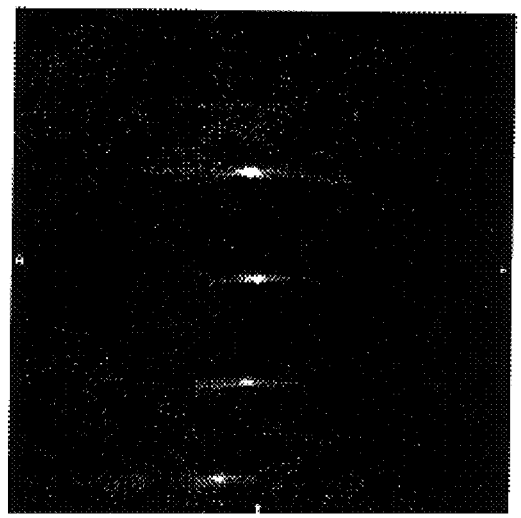
FIG. 7 is a view in partial axial section of the simulation device.
Figure 8:
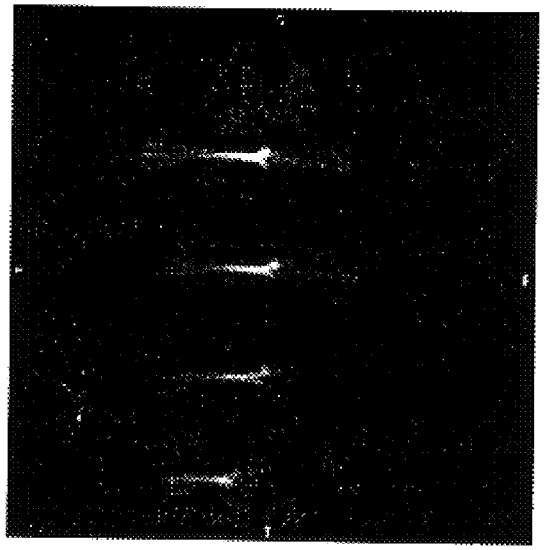
FIG. 8 is a view similar to FIG. 7 with an error in the repositioning of the camera of the X-ray apparatus.

FIG. 7 shows several bright spots corresponding to wires sectioned transverse to their axes. The image of these wires is approximately circular, which is satisfactory. Conversely, in FIG. 8, the image of the same wires tends to spread out, forming a segment of a straight line, which reveals a repositioning error in the rotation of the camera of the image acquisition system, this error being on the order of several tenths of a degree.

As a result, a slight degradation in the performance of the acquisition system produces a visible degradation in the three-dimensional reconstruction of the simulation device. This simulation device can therefore be used to estimate the quality of the three-dimensional image reconstruction of a system. A synthetic view of the quality of the reconstruction can be obtained from the three-dimensional image using a two-dimensional view corresponding to FIG. 4 such that the display is produced parallel to the axis of the central shaft. Certain errors of the acquisition system produce specific errors in the three-dimensional image. The simulation device can therefore be used to characterize image quality problems. The simulation device can be used for a visual inspection by an operator or for an automatic process allowing a quantitative evaluation of the quality of the three-dimensional reconstruction.

This process can be carried out by detecting the central shaft using a series of steps for eroding and enlarging the image, by determining the density of the central shaft, by determining a series of elementary densities obtained by predetermined linear coefficients, by applying a threshold to each elementary density, by creating a two-dimensional image in an orientation parallel to the central shaft, by detecting and counting the wires visible in the image, the final quality criterion being the sum of all the visible wires.

Various modifications in structure and/or function and/or steps can be made by one skilled in the art to the disclosed embodiments without departing from the scope of the invention.

What is claimed is:

1. Device for simulating a patient's body for the testing of a vascular X-ray apparatus of the type comprising means for emitting an X-ray beam, and means for receiving the X-ray beam after it has passed through a part of the patient's body, the X-ray beam being centered on an axis and rotatable, wherein the device comprises at least one metal wire disposed at least partially transversely relative to the axis.

2. Device according to claim 1, wherein the wire is disposed helicoidally relative to an axis normal to the plane of rotation of the axis of the X-ray beam.

3. Device according to claim 1, wherein each wire is disposed on a spire.

4. Device according to claim 2, wherein each wire is disposed on a spire.

5. Device according to claim 1, wherein the wires have diameters that are different from one another.

6. Device according to claim 1, wherein each wire is disposed at a distance from the axis normal to the plane of rotation of the axis of the X-ray beam that is different from that of the other wires.

7. Device according to claim 1, wherein each wire is disposed on a support with a shape adapted to the shape of the means for receiving the X-ray beam.

8. Device according to claim 7, wherein the support has a polygonal equatorial section.

9. Device according to claim 7, wherein the support comprises elements with low X-ray absorption to which the wires are attached, the elements extending from one end of the support to the other.

10. Device according to claim 8, wherein the support comprises a central shaft perpendicular to the axis and made of a material with average X-ray absorption.

11. Device according to claim 9, wherein the support comprises a central shaft perpendicular to the axis and made of a material with average X-ray absorption.

\* \* \* \* \*